United States Patent
Sjoquist et al.

(10) Patent No.: US 9,585,786 B2
(45) Date of Patent: Mar. 7, 2017

(54) REVERSIBLE CONTRACEPTIVE IMPLANT SYSTEM AND METHOD

(71) Applicant: AMS Research, LLC, Minnetonka, MN (US)

(72) Inventors: Scott L. Sjoquist, Minnetonka, MN (US); James A. Alexander, Excelsior, MN (US); Benjamin Y. Arcand, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 211 days.

(21) Appl. No.: 14/214,131

(22) Filed: Mar. 14, 2014

(65) Prior Publication Data

US 2014/0261446 A1    Sep. 18, 2014

Related U.S. Application Data

(60) Provisional application No. 61/783,890, filed on Mar. 14, 2013.

(51) Int. Cl.
*A61F 6/20* (2006.01)
*A61F 6/22* (2006.01)
*A61F 6/02* (2006.01)

(52) U.S. Cl.
CPC .......... *A61F 6/206* (2013.01); *A61F 6/02* (2013.01); *A61F 6/202* (2013.01); *A61F 6/204* (2013.01); *A61F 6/22* (2013.01)

(58) Field of Classification Search
CPC ...... A61F 6/00; A61F 6/02; A61F 6/20; A61F 6/202; A61F 6/204; A61F 6/206; A61B 17/12; A61B 17/122; A61B 17/1227
USPC ......... 128/842, 843; 606/141, 157, 135, 136
See application file for complete search history.

(56) References Cited

U.S. PATENT DOCUMENTS

| | | | |
|---|---|---|---|
| 3,699,957 A * | 10/1972 | Robinson | A61F 6/24 128/843 |
| 3,726,279 A * | 4/1973 | Barefoot | A61B 17/11 606/151 |
| 2009/0131959 A1* | 5/2009 | Rolland | A61F 2/04 606/158 |

* cited by examiner

*Primary Examiner* — Alireza Nia
*Assistant Examiner* — Keri J Nelson
(74) *Attorney, Agent, or Firm* — Bookoff McAndrews, PLLC

(57) ABSTRACT

A contraceptive or occlusion system for restricting and later opening up a reproductive tract or lumen of the vas deferens. The system is adapted to be reversible after implantation, including implantation on, around or within the vas deferens. A method and system to reconnect a severed body lumen, such as the vas deferens, is also provided.

20 Claims, 26 Drawing Sheets

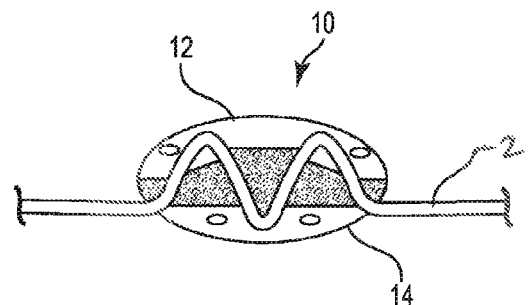
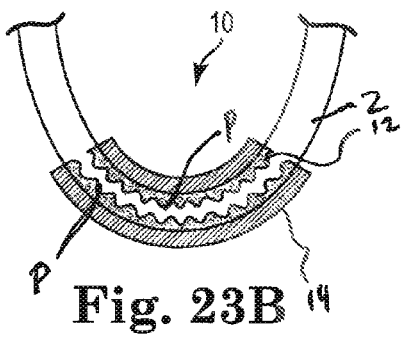
Fig. 23A  Fig. 23B
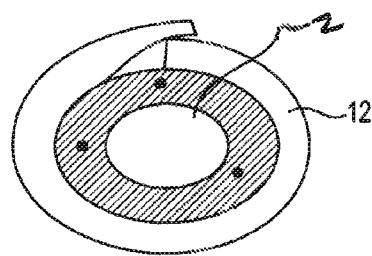
Fig. 24
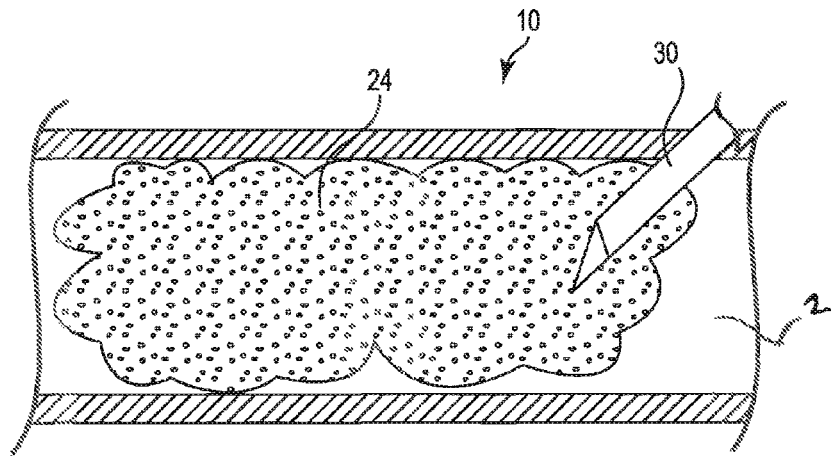
Fig. 25

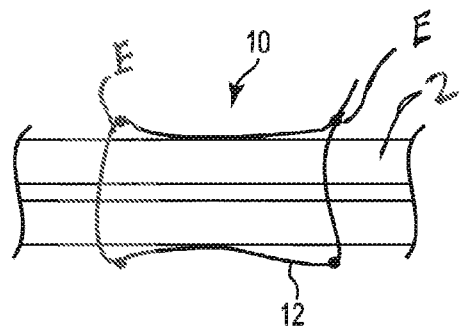
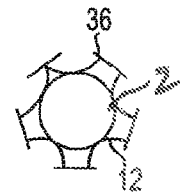
Fig. 26A    Fig. 26B
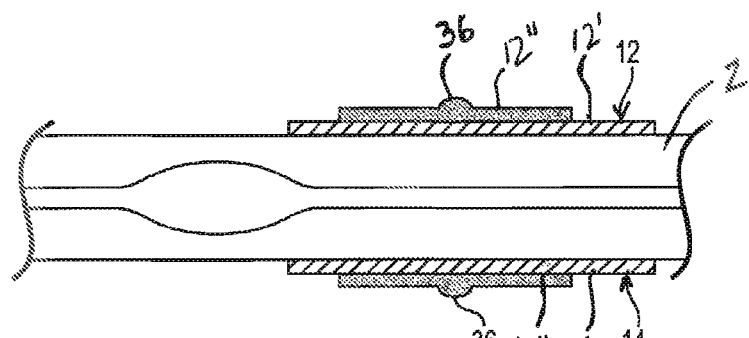
Fig. 27
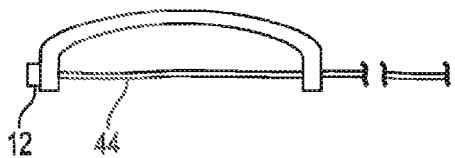
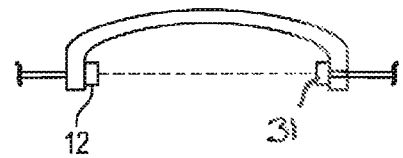
Fig. 28A    Fig. 28B
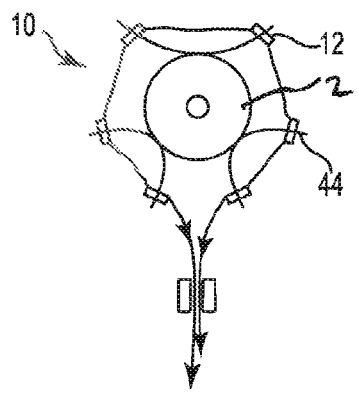
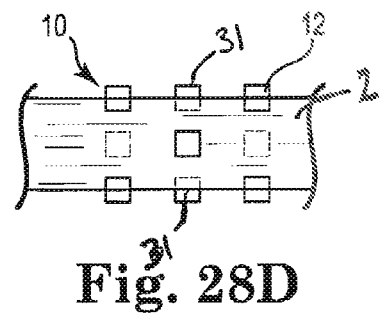
Fig. 28C    Fig. 28D

REVERSIBLE CONTRACEPTIVE IMPLANT SYSTEM AND METHOD

PRIORITY

This Application claims priority to and the benefit of U.S. Provisional Patent Application No. 61/783,890, filed Mar. 14, 2013, which is hereby incorporated fully by reference herein.

FIELD OF THE INVENTION

The present invention relates generally to the field of pelvic implants and, more particularly, reversible contraceptive implants adapted to control the flow of sperm through the vas deferens.

BACKGROUND OF THE INVENTION

One form of contraception involves the occlusion of reproductive tracts, particularly, the fallopian tubes in female subjects and the vas deferens in male subjects, with an embolic material and/or occluding device that acutely and/or chronically (following foreign body tissue reaction or epithelialization) blocks passage of sperm through the reproductive tract. Particular forms of occluding devices and systems and methods of inserting the occluding devices in the vas deferens or fallopian tubes are described in commonly owned U.S. Pat. Nos. 6,096,052 and 6,432,116 and in commonly assigned U.S. Patent Application Publication Nos. 2001/0041900, 2005/0045183, 2005/0085844, 2005/0192616, 2005/0209633, and 2006/0009798, for example, certain features of which are embodied in the Ovion® permanent contraceptive system sold by the assignee of the present invention. Various contraceptive devices and delivery systems disclosed in U.S. Patent Application Publication Nos. 2005/0045183, 2005/0209633, 2006/0009798 and 2008/0308110, as well as PCT Patent Application Publication No. 2007/133222 can be employed, in whole or in part, with the present invention. As a result, each of the above-identified disclosures and publications is incorporated herein by reference in its entirety.

The vasectomy is the most common contraceptive procedure performed in males. There are about 60,000 vasectomy reversals performed each year. The procedure involves severing the vas deferens. A vasectomy may be reversed and is commonly accomplished by suturing the two ends of the vas deferens back together. This procedure usually requires the physician 2-4 hours in the operating room working under a microscope. It would be desirable to provide contraceptive systems that provide improved delivery and deployment systems, and implant structures.

SUMMARY OF THE INVENTION

The present invention is directed to a contraceptive or occlusion system for restricting or opening up a reproductive tract or lumen to prevent the passage of reproductive cells therethrough. Embodiments of the system are adapted to be reversible after implantation.

In one embodiment, the system can include one or more clamp devices provided on or around an external portion of the vas deferens in order to obtain sufficient clamping or restriction strength to deform the wall and occlude the lumen. Other embodiments can include a separation or dissection of the vas deferens such that the implant can be placed in line with the lumen. As such, the implant houses a material to occlude the passage of sperm through the vas deferens.

Yet another embodiment can include any of the disclosed implant devices, combined with sutures or clips selectively provided around a portion of the vas deferens to provide a level of constriction to occlude the flow of sperm through the lumen. The suture can be later cut away to regain the flow of sperm through the implanted device.

An introducer device or delivery system can be used to position and deploy the one or more implant devices at the vas deferens of the patient. Various embodiments of the implant devices can include structures, gels, frames, coatings and like materials or constructs to promote attachment.

Embodiments of the present invention are directed to a device and method to reverse a vasectomy. In one embodiment, the system can include one or more sleeve devices provided on or around an external portion of the vas deferens in order to align the two ends of the vas deferens and a device provided in or around the internal portion of the vas deferens. Other embodiments can include placing caps or like constructs over each end of the vas deferens to reconnect each end. The present invention may be made from materials such as braided material, polypropylene, metals, and others.

Yet another embodiment can include any of the disclosed implant devices, combined with sutures or clips selectively provided around a portion of the vas deferens to provide a method to reconnect each end of the vas deferens.

Various contraceptive devices and delivery systems disclosed in U.S. Patent Application Publication Nos. 2005/0045183, 2005/0209633, 2006/0009798 and 2008/0308110, as well as PCT Patent Application Publication No. 2007/133222 can be employed, in whole or in part, with the present invention. As a result, each of the above-identified disclosures and publications is incorporated herein by reference in its entirety.

BRIEF DESCRIPTION OF THE DRAWINGS

FIGS. 17-36d show restrictive and/or clamping contraceptive type implant systems, in accordance with embodiments of the present invention.

DETAILED DESCRIPTION OF PREFERRED EMBODIMENTS

In the following detailed description, references are made to illustrative embodiments of methods and apparatus for carrying out the invention. It is understood that other embodiments can be utilized without departing from the scope of the invention. Preferred methods and apparatus are described for restriction or occlusion of reproductive body lumens to affect contraception.

It will be understood that the term "contraceptive device," "occlude," "occluding device," "implant," "clamp," "clamp device," "occluding implant" or "occluding member" encompass any type of a device adapted to be delivered at, on, in or around a reproductive tract or lumen to acutely and/or chronically occlude the reproductive tract lumen, including the vans deferens 2.

Referring generally to FIGS. 1-48, a contraceptive implant or reversal system 10 is provided. The system 10 can include one or more clamp devices 12, 14 provided on or around an external portion of the vas deferens 2 in order to obtain sufficient clamping or restriction strength to deform the wall and occlude the lumen.

Figure 1:
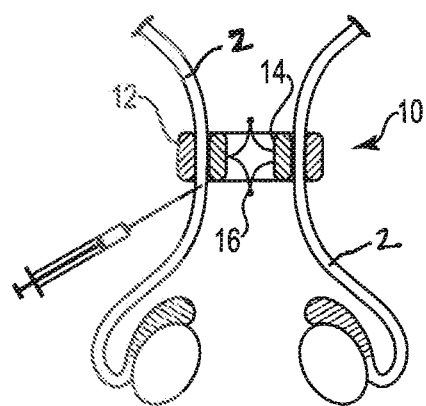
FIGS. 1-4*b* show contraceptive clamping type implant systems provided around the vas deferens, in accordance with embodiments of the present invention.
Figure 2A:
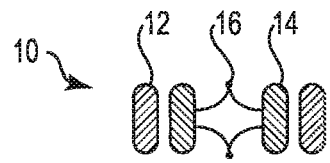
Figure 2B:
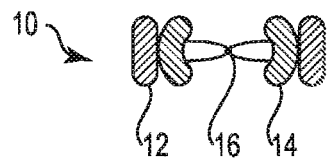

The embodiments of FIGS. 1-2b depict the implant system 10 having a first clamp device 12 and a second clamp device 14. Further, a central control portion 16 is included in operable communication with the first and second clamping device 12, 14. The first and second clamping device 12, 14 are disposed around each vas deferens 2 of the patient. As such, activation or adjustment of the control portion 16 provides selective restriction or collapse of the clamping device 12, 14 to occlude the vas deferens and, thereby, prevent or restrict the flow of sperm through the lumens. For instance, the central control portion 16 can be compressed or adjusted together (FIG. 2b) so the clamp devices 12, 14 around the vas deferens 2 constrict or compress the lumen to restrict fluid flow. To reverse the occlusion, the central control portion 16 can be expanded or otherwise adjusted to withdraw the clamping devices 12, 14 from their restricted position to again allow sperm to flow through the lumens of the vas deferens 2. Other devices, mechanisms and techniques (e.g., fluid, mechanical, electrical, or manual) can be employed with the system 10 to selectively control the clamping or release of the clamping devices 12, 14 in accordance with the procedures disclosed herein.

Figure 3:
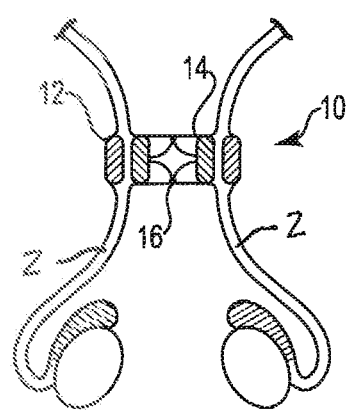
Figure 4A:
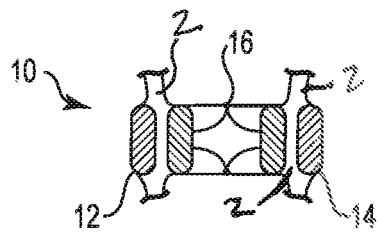
Figure 4B:
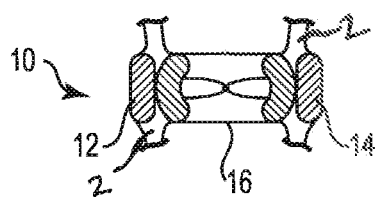

The embodiment of FIGS. 3-4b can include first and second clamp devices 12, 14 adapted for at least partial insertion within the lumen of the vas deferens 2. The central control portion 16 can be positioned intermediate, or even within, the vas deferens 2. As such, the adjustment or actuation of the central control portion 16 closes the clamp devices 12, 14 (FIG. 4b) within the lumen to occlude the lumen and restrict the flow of sperm therethrough.

Figure 5:
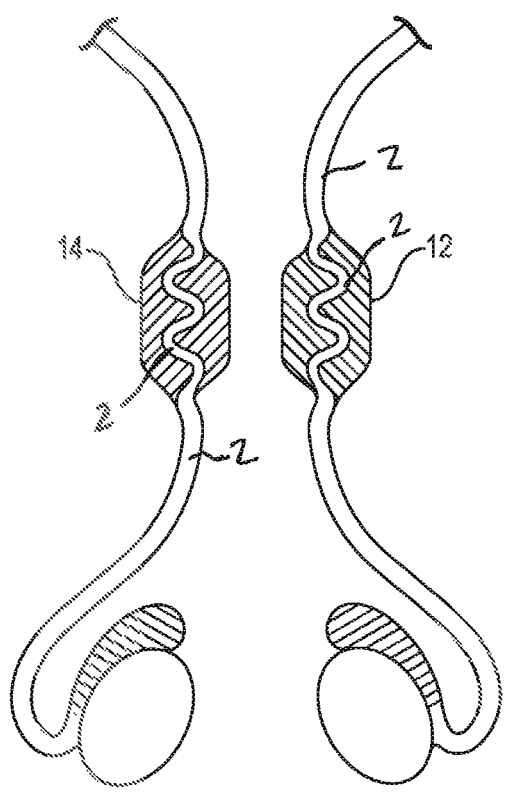
FIGS. 5-6*b* show contraceptive implant systems with tunnels therein adapted to receive a portion of the vas deferens, in accordance with embodiments of the present invention.
Figure 6A:
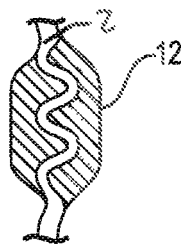
Figure 6B:
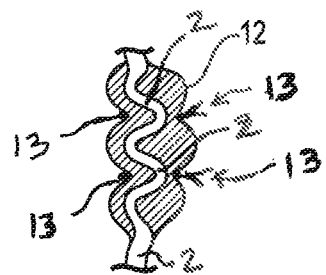

The embodiment of FIGS. 5-6b may include a first and second clamping device 12, 14 provided around a portion of the vas deferens 2 (FIG. 6a), to provide a level of constriction to occlude the flow of sperm through the lumen. The clamping devise may optionally alter the vas deferens lumen 2. If additional pressure is needed, sutures 13 can be tied around the first and second clamping devices 12, 14 (FIG. 6b). The clamping mechanism 12 can be later cut away to regain the flow of sperm through the implanted device.

Figure 7:
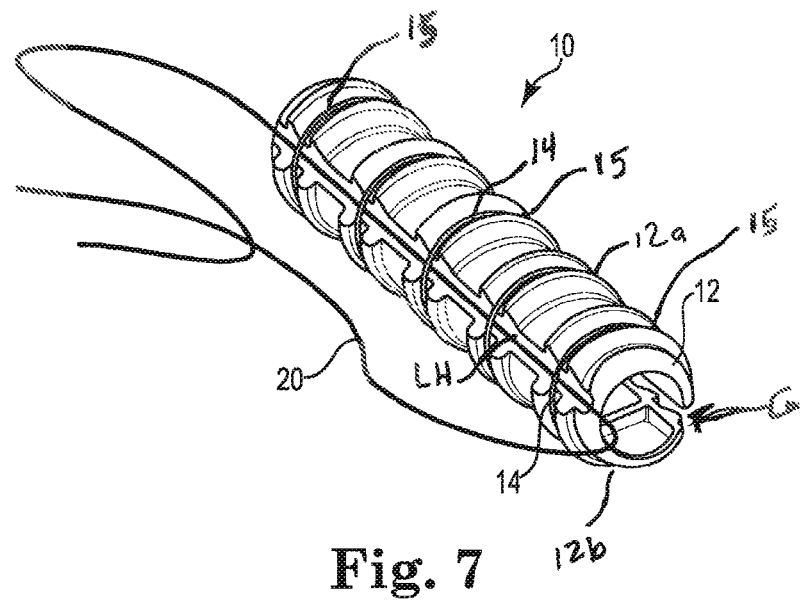
FIGS. 7-8 show a contraceptive implant system having hingable tubular devices adapted to surround a portion of the vas deferens, in accordance with embodiments of the present invention.
Figure 8:
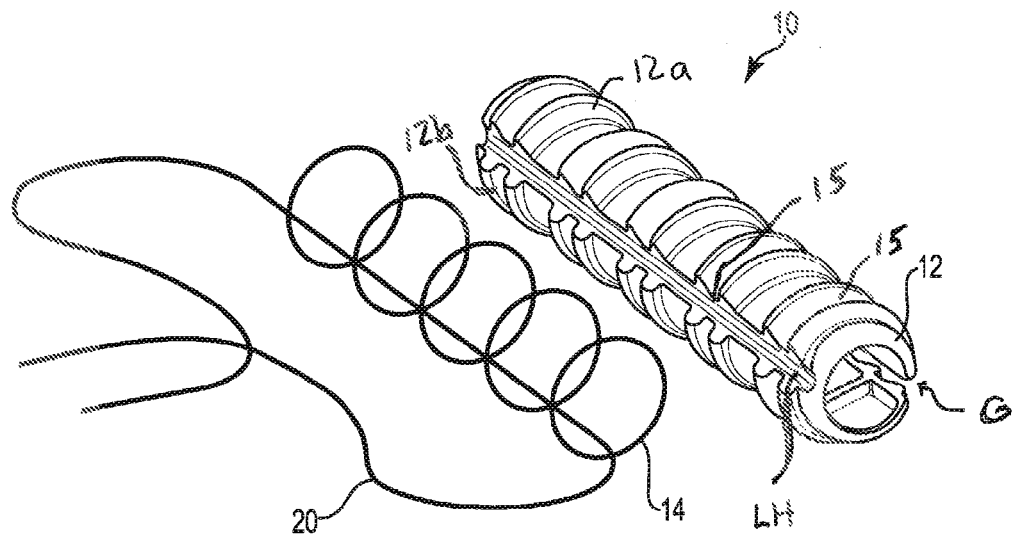

FIGS. 7-8 depict an exemplary multi-piece embodiment of an implant 10 adapted to restrict sperm flow through the lumen of the vas deferens 2. A first clamping mechanism 12 is disposed around the vas deferens 2 to provide support for a second clamping device 14. The mechanism 12 can be constructed of first and second portions 12a, 12b and may be made of a biocompatible material such polypropylene or other flexible material. A gap G can be provided along a longitudinal length of the mechanism 12 such that a degree of opening or closing of the lumen diameter, about living hinge LH, is available via tightening or loosening of a second clamping device 14. The clamping mechanism 12 can later be removed via a releasing member 20 which can be threaded through the second clamping device 14.

Second clamp device 14 may be in the form of a suture, Nitinol or like coil or shape memory material provided or wrapped in grooves or like surface features 15 of the mechanism 12 to provide selective pressure on the vas deferens 2. The second clamping device 14 can be integrated with the first clamping device 12, or can be provided as a separate component. Releasing mechanism or member 20 allows for a single incision removal of device 10. The device 10 may be provided with the second clamping device 14 already disposed upon the first clamping device 12. In certain embodiments, the releasing member 20 is a suture or like material or device that can be pulled or otherwise disposed to release from the mechanism 12 and, therefore, release pressure on or eliminate occlusion of the vans deferens 2.

Figure 9:
FIGS. 9-10 show a contraceptive implant system being generally coil shaped, in accordance with embodiments of the present invention.
Figure 10:
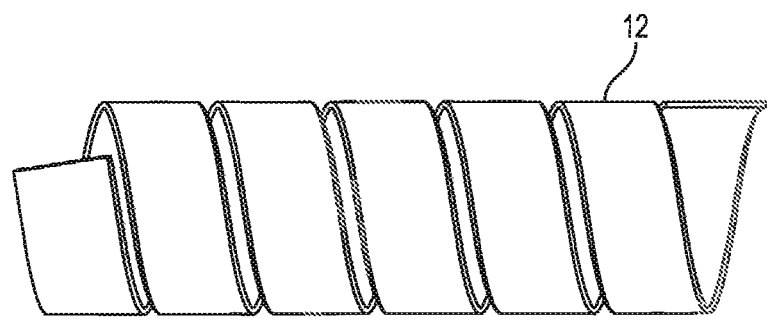

FIGS. 9-10 illustrate an embodiment of a first clamp device 12. First clamp device 12 is composed of Nitinol or like material that has two stable configurations. The first stable configuration is substantially straight, which provides little to no pressure on the vas deferens 2 and allows for implantation and explantation of the device 10. The second stable configuration forms a coil or spring-like construct that can be disposed around the vas deferens 2, wherein the coil provides pressure on the vas deferens 2. The first clamping device 12 may be coiled around the vas deferens about 3 to 5 times in certain embodiments. A variety of other shapes, sizes and coil configurations are envisioned for alternative embodiments as well.

Figure 11:
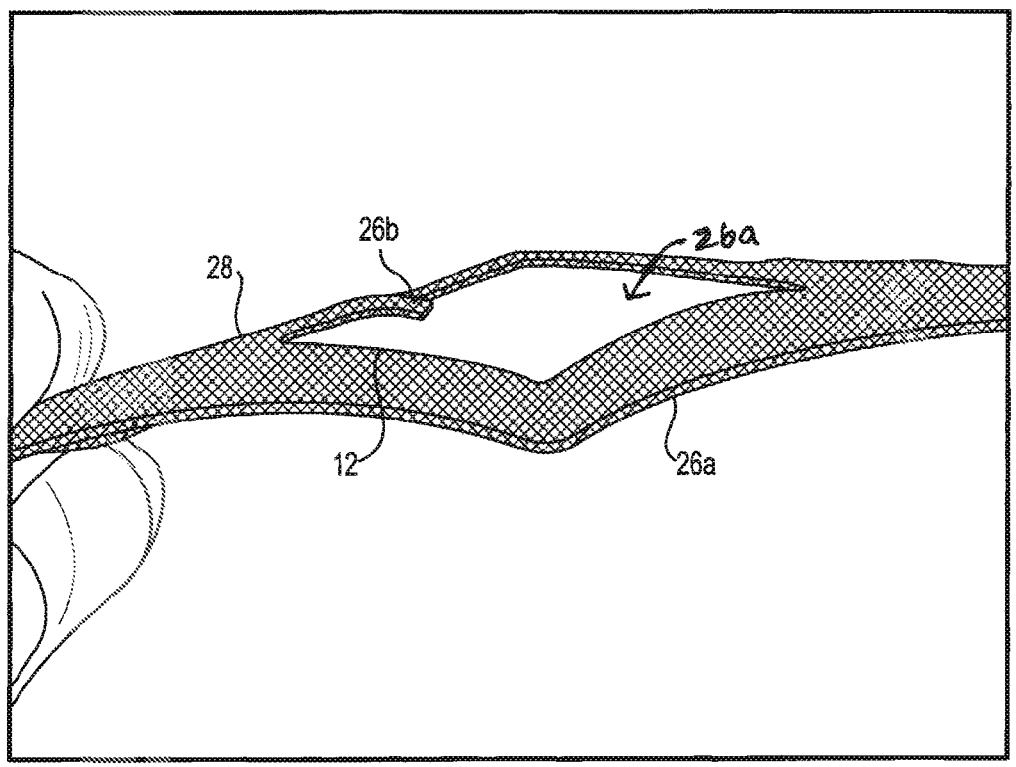
FIG. 11 shows a contraceptive implant system adapted to apply pressure around a portion of the vas deferens, in accordance with embodiments of the present invention.

FIG. 11 illustrates another embodiment of an implant 10. The first clamp device 12 is comprised of at least two arm portions 26a, 26b proximally connected at a base 28, wherein the at least two arms 26a, 26b are positionable opposite each other around such that an opening 26c is provided to surround a portion of the vas deferens 2. The first clamp device 12 may have two configurations wherein the 'open' configuration allows the device to be placed around the vas deferens 2 and the 'closed' configuration provides pressure on the vas deferens 2. The device 12 can be constructed of a mesh, polymer, metal, or like material.

Figure 12:
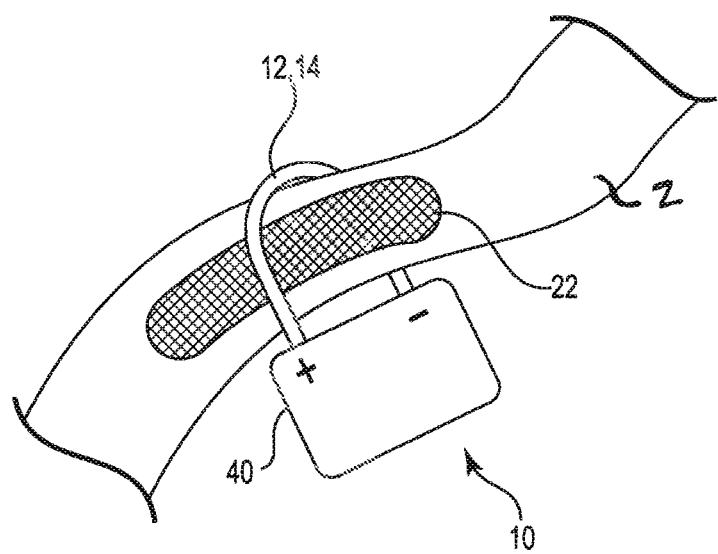
FIGS. 12-13 show a contraceptive implant system having one or magnets, in accordance with embodiments of the present invention.
Figure 13:
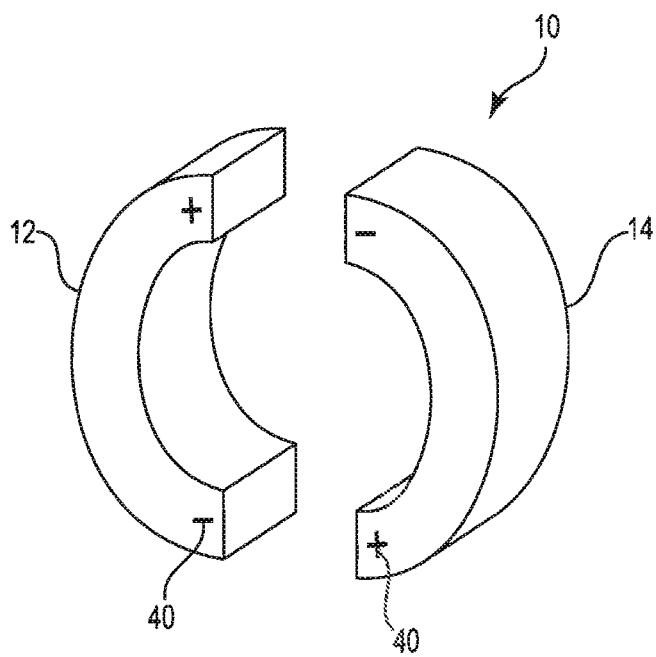

An implant system 10 may contain one or more magnets 40 as shown in FIGS. 12-13, disposed around the outside of the vas deferens 2. In one embodiment, the vas deferens 2 can be injected with a ferrous-containing material 22 (e.g., fluid). Upon placing the implant system 10 around the vas deferens 2, the magnets 40 attract the ferrous-containing material 22 which forms a bolus, thereby occluding the body lumen. The ferrous-containing fluid 22 liquefies once the implant system 10 containing magnets 40 are removed, and vas deferens 2 function (fluid passage) is restored. In the alternative, a first clamp device 12 and second clamp device 14 containing one or more magnets 40 may be placed around the vas deferens 2, as shown in FIG. 13. When the magnets 12, 14 are in close proximity to each other pressure is applied to the vas deferens 2. Occlusion of the vas deferens 2 is eliminated by removing the first and second clamping devices 12, 14.

Figure 14:
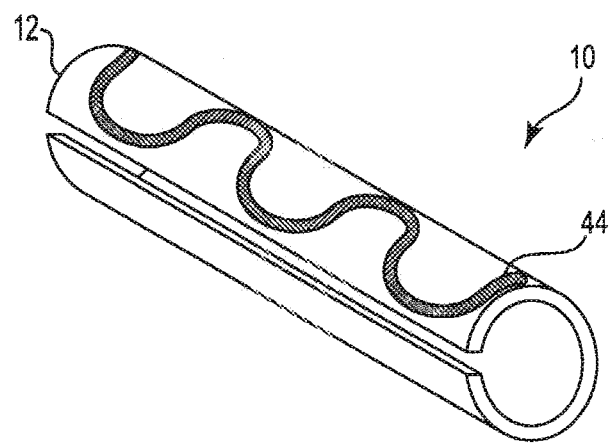
FIG. 14 shows a generally tubular contraceptive implant system, in accordance with embodiments of the present invention.

FIGS. 14-20 show various embodiments of an implant system 10. A first clamping device 12 may be a silicone stent with nitinol wire 44 molded inside the silicone (FIG. 14). The wire 44 can be integrated with the device 12 or otherwise provided separately. A gap G is provided along a longitudinal length of the device 12 such that selective pressure on the vas deferens 2 is available upon deployment and actuation.

Figure 15:
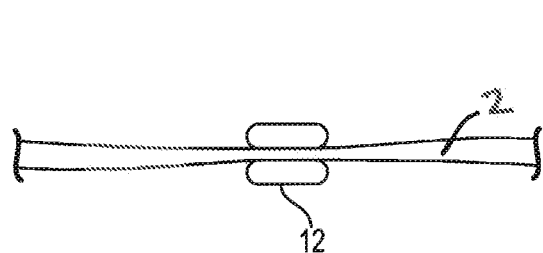
FIGS. 15-16 show restricting contraceptive implant systems, in accordance with embodiments of the present invention.
Figure 16:
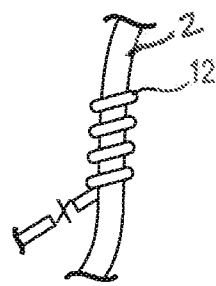

FIGS. 15 and 16 show an embodiment wherein the first clamp device 12 can be a pressurized cuff or cuff member that encircles a portion of the vas deferens 2 one or more times. The first clamp device 12 may be pressurized to a pressure of about 1 to 2 pounds per square inch (psi), or from about 1.25 to 1.5 psi. Other pressure and application configurations are envisioned for various other embodiments. Once applied, an extending free end or portion of the device can be cut away or otherwise removed (FIG. 16)

Figure 17:
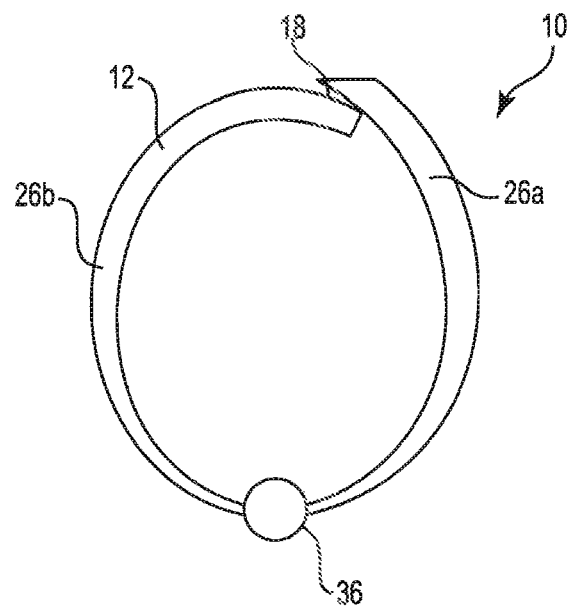

FIG. 17 illustrates a first clamp device 12 that contains two arms 26a, 26b, a joint or hinge portion 36 and a clamping portion 18. The joint 36 is located between the two arms 26a, 26b. The joint 36 may open for placement and removal around the vas deferens 2. Alternatively, the joint 36 may be removed from the first clamp device 12 for removal. The clamping portion 18 can include an overlapping lip, a clip, a clasp, or like devices or mechanisms.

Figure 18:
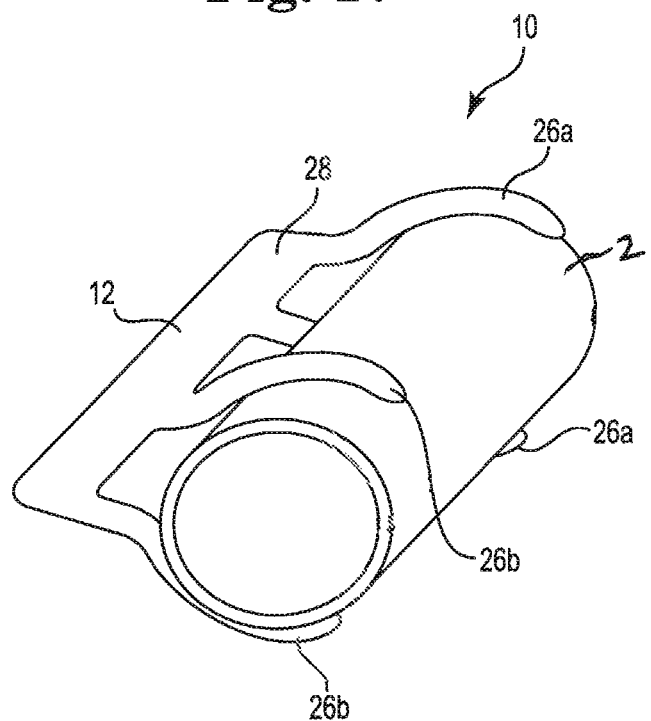

FIG. 18 shows a first clamp device 12 that contains four arms 26a, 26b, 26a', 26b' that extend from a base 28 and wrap around the vas deferens 2. The base 28 can be located at an approximately equal distance between the arms 26a, 26b. The arms 26a, 26b have a relaxed and constricted configuration. The constricted configuration puts pressure on the vas deferens 2 while the relaxed configuration is used for insertion and extraction of the implant. Portions of the device 12, including the arms, can be constructed of a polymer or metal material capable of being manipulated to selectively achieve the various relaxed and constricted states.

Figure 19:
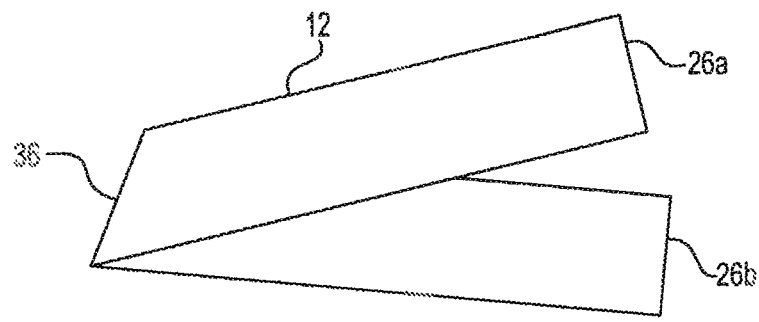

FIG. 19 illustrates an alternative embodiment of an implant 10 that contains two arms 26a, 26b connected at a joint or hinge portion 36 that slide into place around the vas deferens 2. The arms 26a, 26b of the first clamping device 12 may hingably move away from each other in a generally planar fashion and orientation to provide selective pressure or release from the vas deferens 2. The arms 26a, 26b can be biased, or can be constructed of a shape memory material, such that they will approach or move toward each other about the joint 36 to apply pressure to the vas deferens 2 upon deployment around the body lumen.

Figure 20:
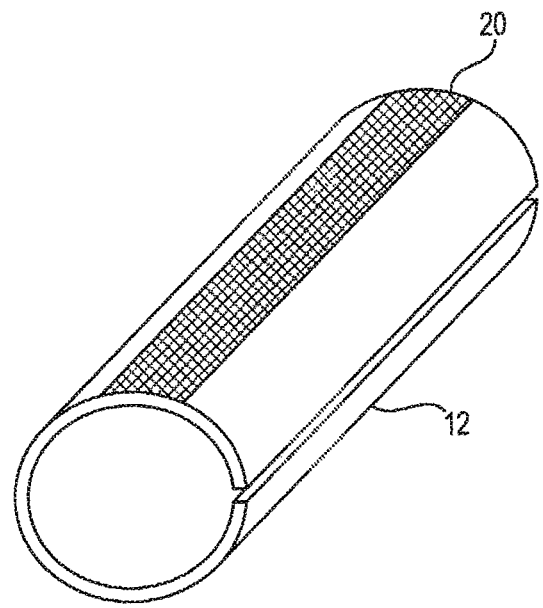

FIG. 20 shows an embodiment of a clamp device 12 that contains a releasing portion 20. The clamping device 12 is shaped to surround the vas deferens 2 and is made from a material stronger and more resilient than that of the releasing portion 20. The releasing portion 20 is positioned lengthwise or longitudinally along the clamping device 12 and is made from an easy to cut material. The releasing portion 20 can be constructed of a polymer material, such as a mesh, and can be measurably expandable or stretchable to accommodate deployment around the vas deferens 2. When removal is desired, the releasing material 20 can be cut away or otherwise removed to reduce or eliminate pressure on the vas deferens 2.

Figure 21:
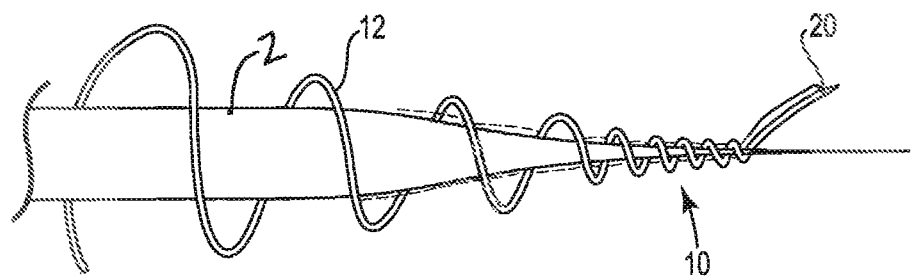

FIG. 21 illustrates another embodiment of an implant 10. The implant 10 has a first clamping device 12 that spirals around the vas deferens 2. The first clamping device 12 may be made from nitinol or other like material. In an open configuration the first clamping device 12 is spiraled loosely around the vas deferens 2 and does not generally provide pressure. In a closed configuration, the first clamping device 12 is wrapped around the vas deferens 2 in a tight spiral, thereby occluding the lumen. When removal is desired, the exposed or free end 20 of the first clamping device 12 eliminates occlusion and acts as a releasing mechanism that can facilitate removal from the body. The end 20 can include knots, clips or other devices, techniques or members to facilitate engagement, securement and eventual disengagement.

Figure 22:
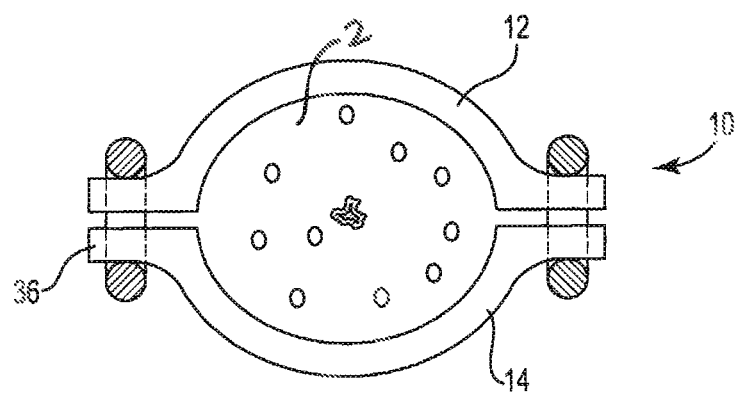

FIG. 22 shows an embodiment of an implant system 10 comprised of a first clamping device 12 and a second clamping device 14. The first and second clamping devices 12, 14 are configured to surround the outer diameter of the vas deferens 2. At least one joint or hinge portion 36 is positioned between the first and second clamping devices 12, 14. The at least one joint 36 may be shaped as a bar, rubber band, or other joint-like or expansion structure, and may include clips, elastic members and the like to facilitate selective closure and/or opening of the joint 36. When occlusion of the vas deferens 2 is desired the joint 36 is closed so that the first and second clamping devices 12, 14 provide pressure. When occlusion is not desired, the joint 36 can be opened.

FIGS. 23a and 23b illustrate yet another embodiment of the implant system 10. FIG. 23a shows an implant system 10 comprised of a first clamping device 12 and a second clamping device 14. The first and second clamping devices 12, 14 are configured to create a snap fit closing around the outer diameter of the vas deferens 2. Within the first and second clamping devices 12, 14 is a generally shaped tunnel lumen wherein the vas deferens 2 is threaded or fed. The tunnel may be shaped as a spiral, chevron, or other similar shape. The tunnel functions to create kinks in the vas deferens 2, which occludes the flow of fluids within the body lumen. FIG. 23b shows an implant 10 wherein the first and second clamping mechanism 12, 14 include protrusions P to create additional pressure points on the vas deferens 2. Again, the vas deferens 2 is threaded through the lumen/tunnel including the protrusions P.

FIG. 24 shows a first clamping device 12, wherein the first clamping device 12 is capable of encircling the vas deferens 2. The first clamping device 12 may be in a constant occlusion state, or may be subject to control by the patient. The patient may be able to release the first clamping device 12 to limit the pressure on the vas deferens 2. An alternative method to release the first clamping device 12 is to create the first clamping device 12 from a heat-sensitive material. When occlusion is desired the resting temperature of the device may be changed by applying heat or cold to facilitate construction and thereby pressure on the vas deferens 2. Alternatively, the device may be sized and shaped to only have one proximal or distal end pressurized at a time. The patient may alter which end is active at any time, thereby reducing potential damage to the vas deferens 2 by having constant pressure on the body lumen. Actuation of the occluding effects can be achieved via temperature change, mechanical, electrical or other means or techniques.

FIG. 25 shows another embodiment of an implant system 10. The implant system 10 includes an insertion tool 30, bulking mechanism or substance 24 and an energy source. The insertion tool 30 is capable of injecting a porous or like bulking mechanism 24 into the vas deferens 2. The bulking mechanism 24 contains pores that are smaller than sperm, allowing other fluids to flow through the bulking mechanism 24, but restricting flow of sperm. Occlusion may be reversed by applying energy that enlarges the pores of the bulking mechanism 24, thereby generally allowing the free flow of fluid. The bulking mechanism 24 may be made from alternative materials, e.g., Botox, which would temporarily paralyze the vas deferens 2 in an occluded state.

FIGS. 26a and 26b illustrate an embodiment of an implant system 10 having at least one clamping device 12 to be placed around the vas deferens 2. A first clamping device 12 may have a generally hammock shape, including a distal, proximal, and middle portion. The middle portion applies pressure to the vas deferens 2 while the distal and proximal ends are connected to corresponding distal and proximal ends E of another clamping device 12 (see FIG. 26b). More than one first clamping device 12 may be utilized and held together at the distal and proximal end by a joint 36 to form a circle-like structure surrounding the vas deferens 2.

FIG. 27 illustrates a first clamping device 12 having a first surface 12' and second surface 12" and a second clamping device 14 having a first surface 14' and second surface 14". The first surfaces 12', 14' of each the first and second clamping devices 12, 14 are in contact with the outer surface of the vas deferens 2. The first and second clamping devices 12, 14 can include a joint 36 at a general middle point. This joint 36 allows a distal end of the first and second clamping devices 12, 14 to contract toward each other with an increase in pressure in the vas deferens 2. If there is no pressure, the joint 36 is opened.

Figure 29:
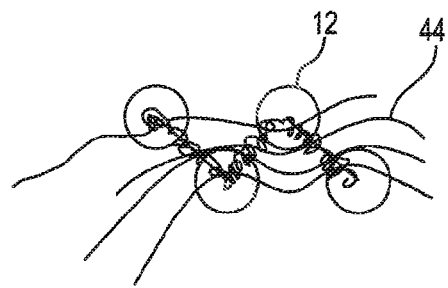
Figure 30:
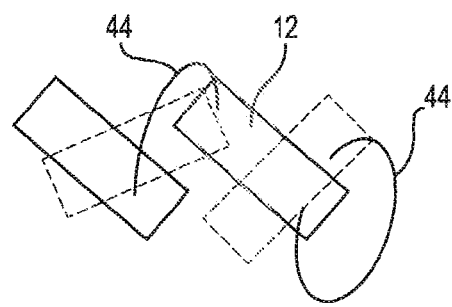

FIGS. 28-30 illustrate another exemplary embodiment of an implant system 10. Multiple first clamping devices 12 may be placed around the outside of the vas deferens 2 at approximately 120° spacing configurations (FIG. 28c). The first clamping devices 12 may be pressure pads 31, or other small pressure point mechanisms such as a pinch wheel (see FIG. 28b). A Nitinol wire 44, or other like material, may be threaded through the first clamping devices 12 in rows of first clamping devices 12 generally transverse to the vas deferens 2 (FIG. 28c). When pressure is desired, the wire 44 may be pulled taut, thereby cinching the implant system 10 (FIG. 28c). Alternatively, as shown in FIG. 29, the first clamping devices 12 may be threaded with a wire 44 in a zigzag or chevron like pattern. When the wire 44 is pulled taut, the first clamping device 12 cinches around the vas deferens 2 in a crossing or like pattern (see FIG. 30).

Figure 31:
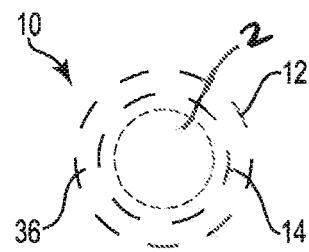

FIG. 31 illustrates an implant system 10 including an outer first clamping device 12 and an inner second clamping device 14. The first and second clamping devices 12, 14 may be shaped as arcs and held together at a joint 36. The clamping mechanism 18 may be a ball-and socket joint or other similar mechanical joint 36 thereby allowing the implant 10 to selectively apply pressure to the vas deferens 2.

Figure 32:
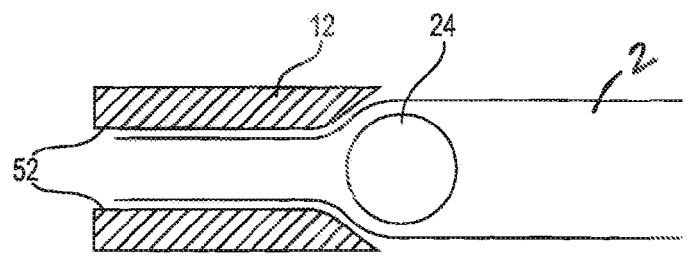

FIG. 32 shows a first clamping device 12 disposed around the outside of the vas deferens 2 and a bulking mechanism 24 provided within the vas deferens 2. The first clamping mechanism 12 has an inner diameter 52 smaller than the diameter of the vas deferens 2 and the bulking mechanism 24 is of a diameter larger than the inner diameter 52 of the first clamping mechanism 12. The flow of fluid pushes the bulking mechanism 24 towards the first clamping mechanism 12, thereby occluding the body lumen. Alternatively, the first clamping device 12 and the bulking mechanism 24 may be attracted to each other, e.g., by a magnet or like device included with each, and with appropriate attracting polarity.

Figure 33A:
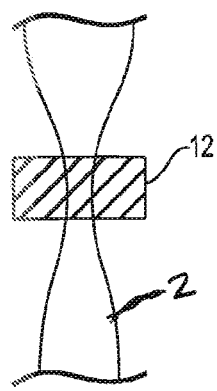
Figure 33B:
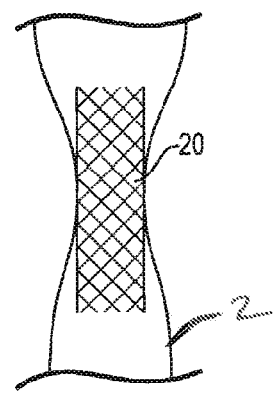

Another embodiment of an implant 10 is shown in FIGS. 33a-33b. A first clamping device 12 uses the natural action and body/lumen movement of the body to create an anastomosis. The first clamping device 12 can be implanted around the vas deferens 2 to cause the lumen to shrink, thereby occluding the vas deferens 2. The first clamping device 12 can be constructed of an absorbable or non-absorbable material. When reversal is desired, a releasing mechanism 20 is deployed within the lumen (FIG. 33b). The releasing mechanism 20 can be in the shape of a stent or other device that works to expand a lumen such as the vas deferens 2. Alternatively, a laser or like device or technique can be used to reopen the closed lumen.

Figure 34A:
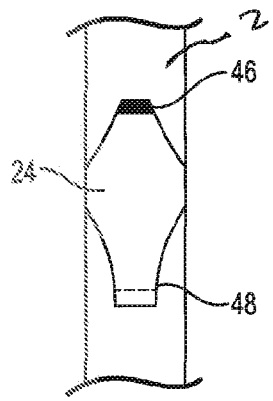
Figure 34B:
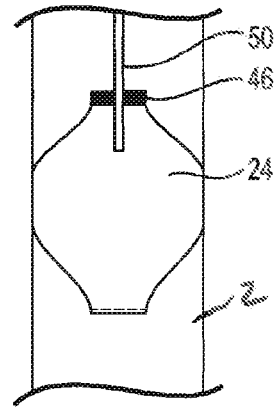
Figure 35A:
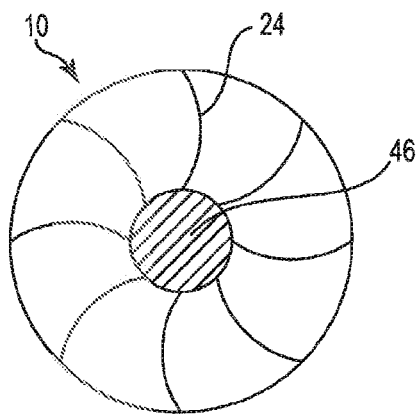
Figure 35B:
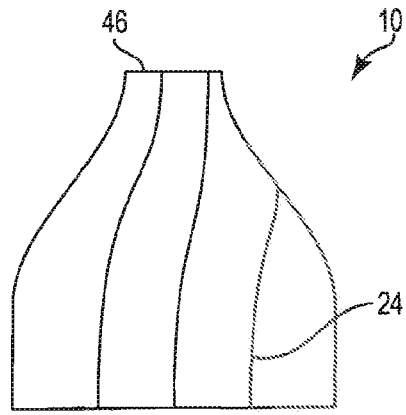
Figure 35C:
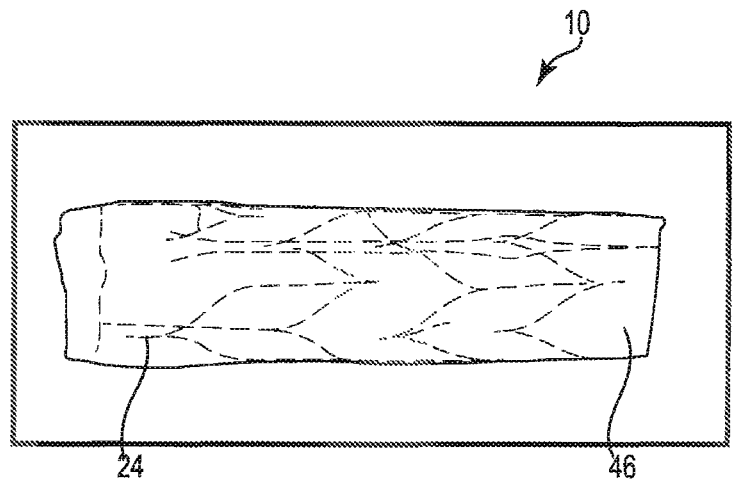
Figure 35D:
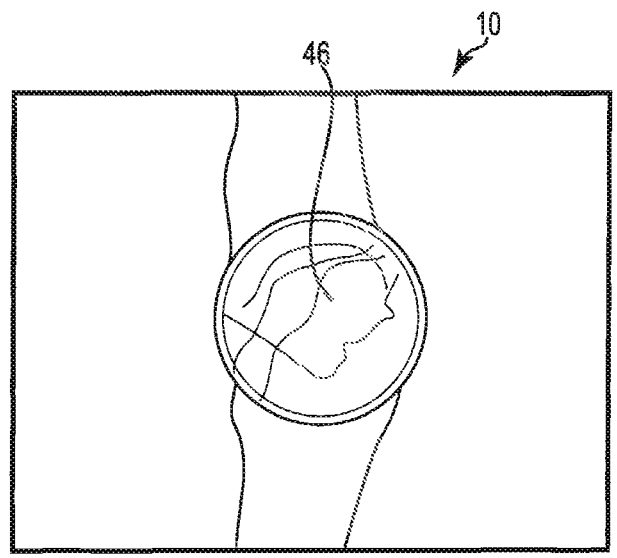
Figure 35E:
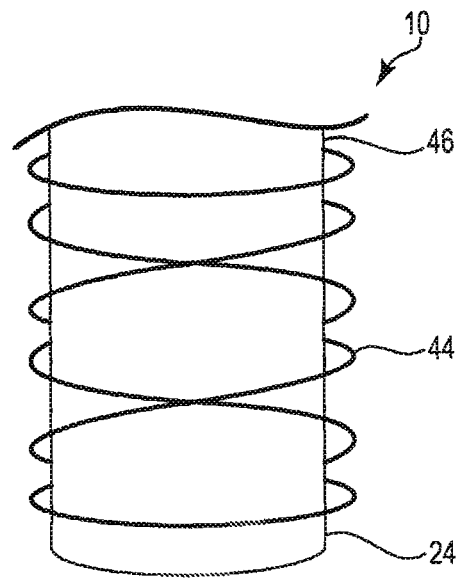
Figure 35F:
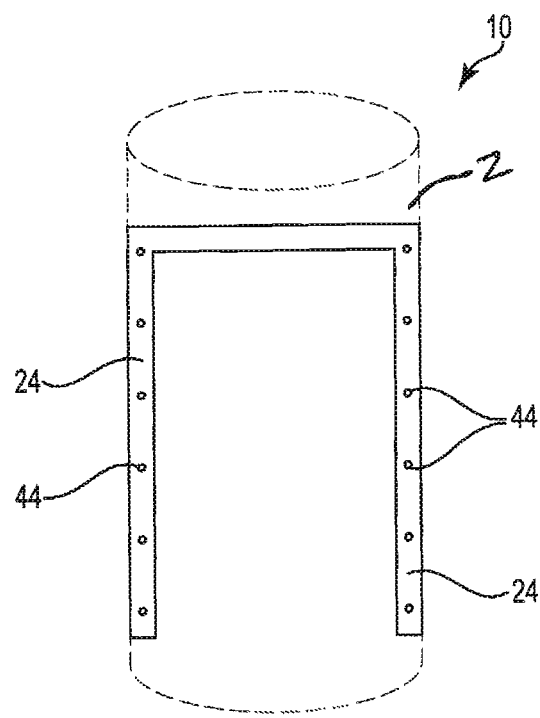

FIGS. 34a-34b illustrate a bulking mechanism 24 disposed within the vas deferens 2. The bulking mechanism 24 may include a membrane 46 on a distal end and an expanding valve 48 on a proximal end. The bulking mechanism 24 can be placed within the lumen of the vas deferens 2 to provide occlusion. When reversal is desired, a needle or like tool 50 can be introduced to pierce the membrane 46 and/or the valve 48, thereby allowing fluids to pass through the vas deferens 2 without having to remove the bulking mechanism 24 (FIG. 34b).

FIGS. 35a-35f illustrate an implant system 10 that is able to feather fit into different diameters or portions of the vas deferens 2. The implant system 10 comprises a central membrane 46 on a proximal end surrounded by a bulking mechanism 24 on the distal end. The length of the implant 10 can be about 0.5 to 1.0 inches, or about 0.65 to 0.75 inches. The diameter of the implant 10 can be about 0.1 to 0.25 inches, or about 0.15 to 0.2 inches. The ends can be square or rounded in shape, or can take on a variety of other shapes and sizes. Once in the body lumen, the membrane 46 can selectively expand to hold the bulking mechanism 24 in place to provide occlusion. A Nitinol or like wire 44 or other like material may be molded or otherwise provided with the bulking mechanism 24 to provide extra support. The implant 10 may be delivered through a catheter-like device. To remove, the proximal end of the bulking mechanism 24 is retrieved and pulled out of the vas deferens 2. The implant 10 can additionally include a surface treatment that kills sperm.

Figure 36A:
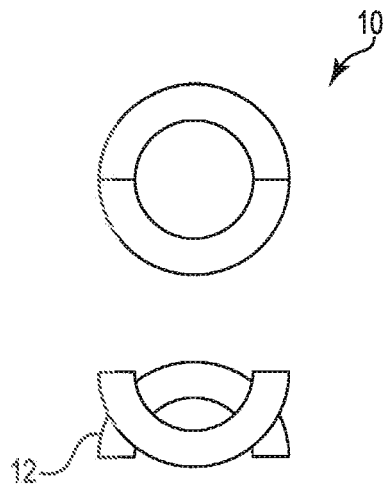
Figure 36B:
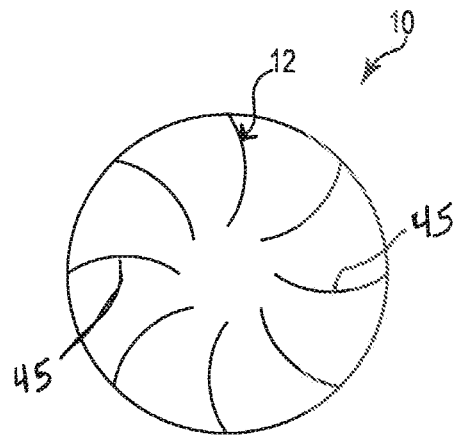
Figure 36C:
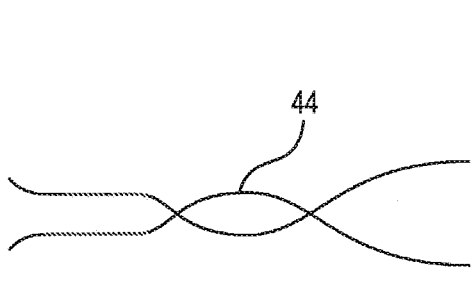

FIG. 36a-36d illustrate an alternate implant 10 to compress the vas deferens 2. Implant system 10 of FIG. 36a comprises of a first clamping mechanism 12 surrounding the outside of the vas deferens 2. FIG. 36b illustrates an implant 10 that comprises a first clamping device 12 wherein the clamping mechanism 12 has protrusions 45 on the inner diameter to provide additional pressure points on the vas deferens. FIG. 36c illustrates a Nitinol or like wire 44 that can compress the vas deferens 2. The wire 44 may be shaped in a chevron or serpentine pattern or braided around the outside of the vas deferens 2 to put pressure on the body lumen.

Figure 36D:
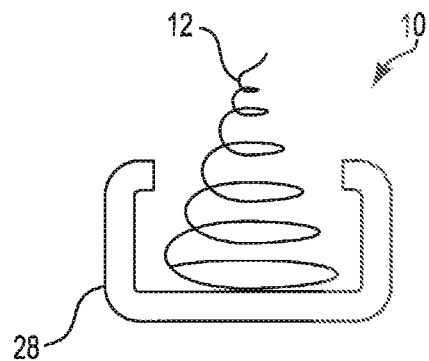

FIG. 36d shows yet another implant system 10 to compress the vas deferens 2. The implant system 10 is comprised of a base 28 that is shaped to surround the outside of the vas deferens 2. A first clamping mechanism 12 is located within the base 28. The clamping mechanism 28 may be a spring-like or helical-like device that puts pressure on the vas deferens 2 when the base 28 is implanted around the vas deferens 2 the first clamping mechanism 12 is situated at the vas deferens 2.

Figure 37A:
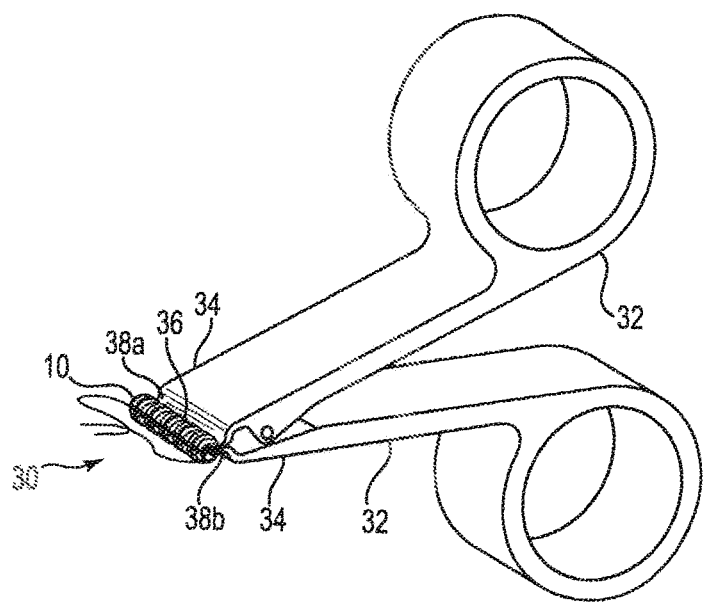
FIGS. 37a-38b show insertion tools for a contraceptive implant system, in accordance with embodiments of the present invention.
Figure 37B:
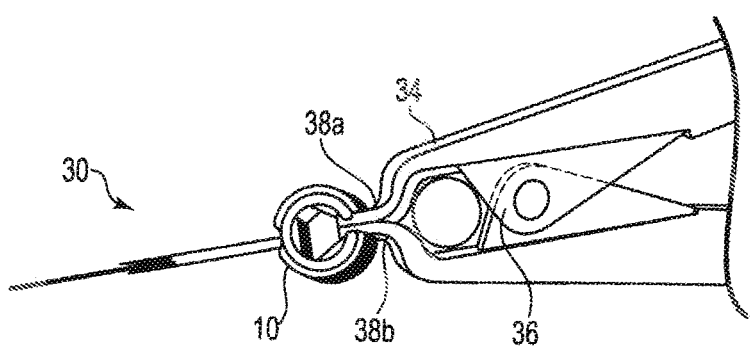
Figure 37C:
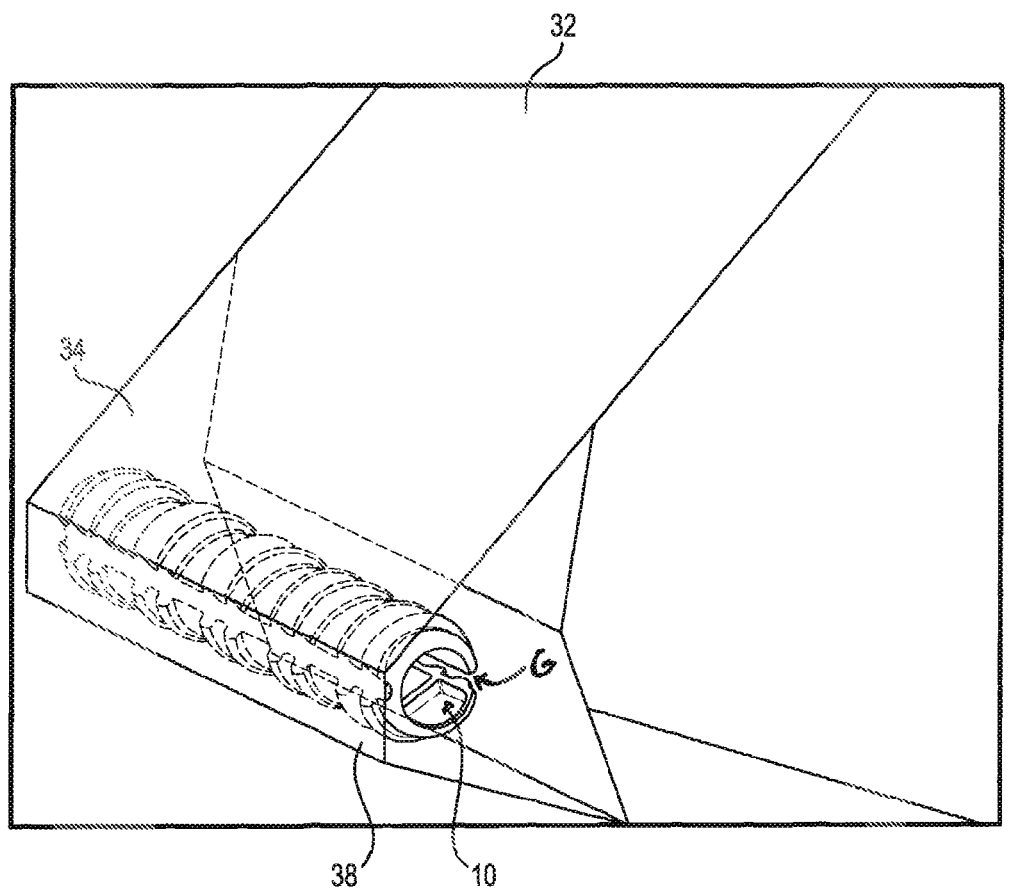

FIGS. 37a-37c show an insertion tool 30 for use with embodiments of the present invention. The insertion tool 30 can include at least one handle 32, shaft 34, hinge joint 36, and upper and lower placement flanges 38a, 38b. The upper and lower placement flanges 38a, 38b operatively connect with implant system 10 for placement or deployment around the vas deferens 2. The joint 36 can be used to hold the device 10 in place while expanding or opening up the device 10 (e.g., at gap G) for placement around the vas deferens 2. The insertion tool 30 may also operatively couple with the inside of the implant system 10 to place around the vas deferens 2.

Figure 38A:
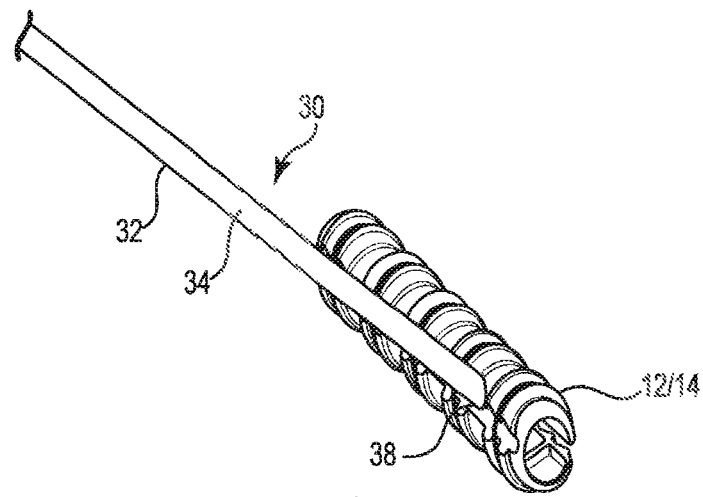
Figure 38B:
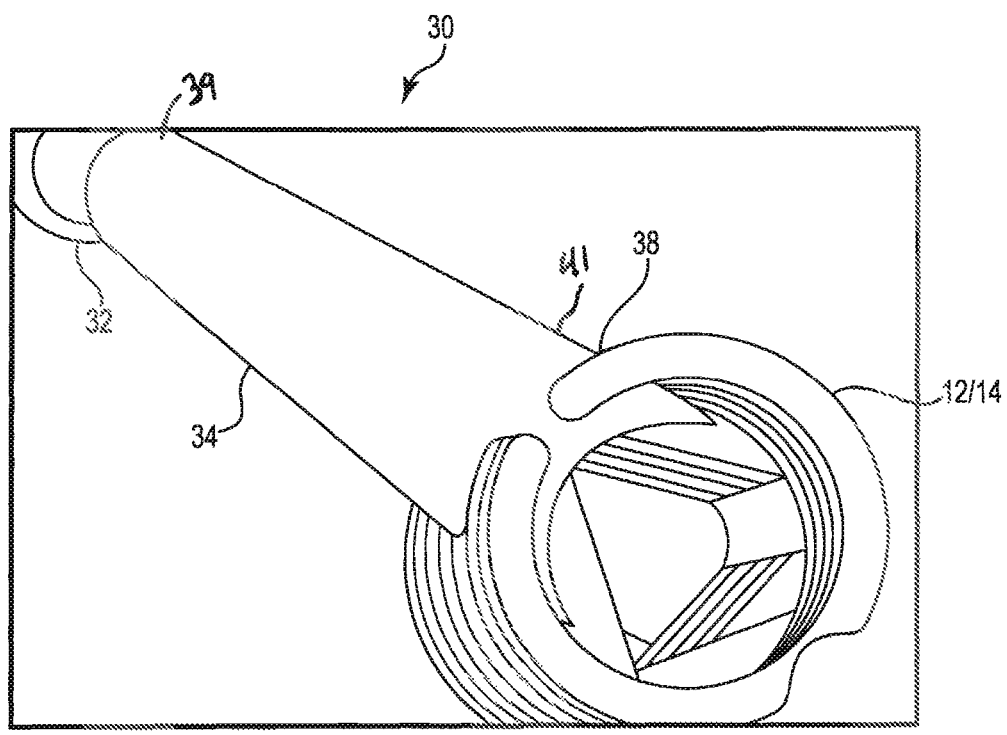

FIGS. 38a-38b illustrate another embodiment of an insertion tool 30. The insertion tool 30 is comprised of a handle 21, shaft 34, and flange 38. The shaft 34 has a proximal end 39 and the flange 38 on the distal end 41. The flange 38 can interlock with the inner diameter of an implant system 10 or portion 12, 14 to aid in implementation around the vas deferens 2.

Figure 39:
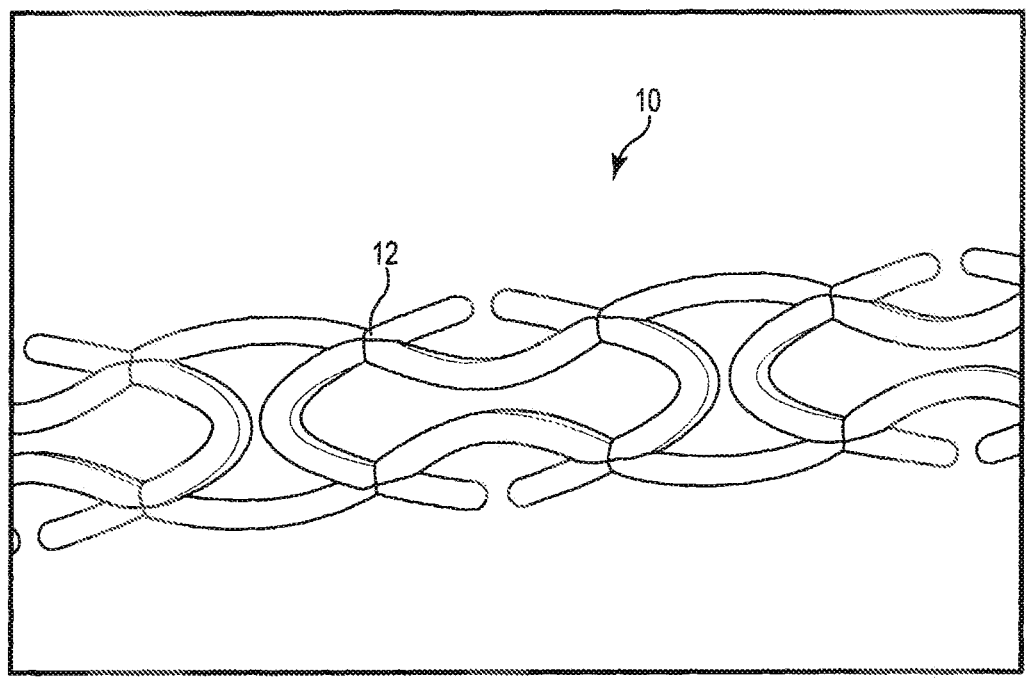
FIGS. 39-48 show systems to aid in reversal of a vasectomy or otherwise repairing a severed or damaged vas deferens, in accordance with embodiments of the present invention.
Figure 40:
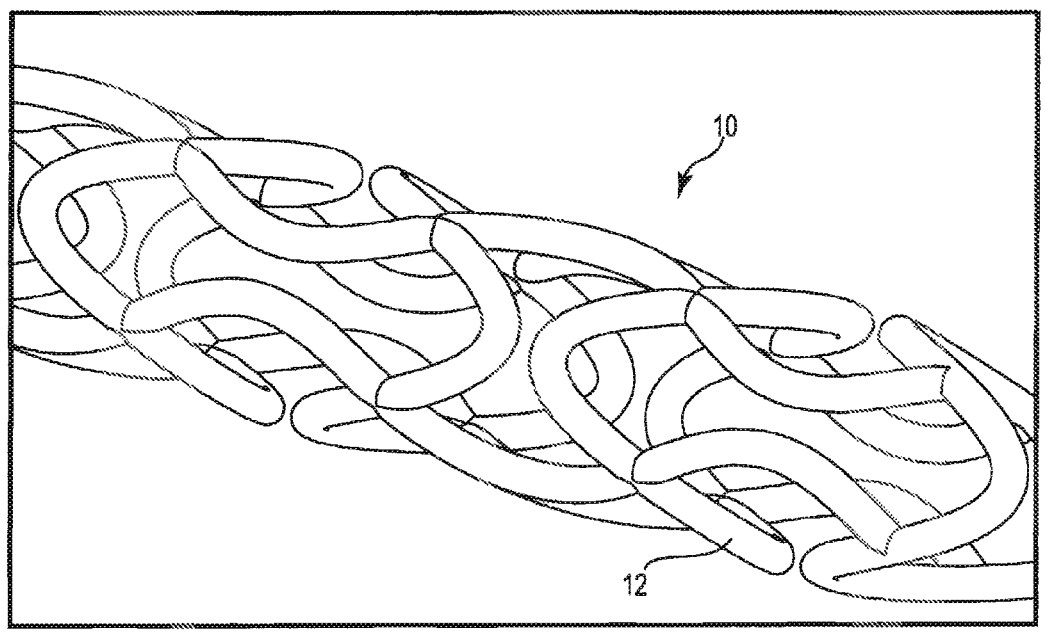

FIGS. 39-40 illustrate an exemplary embodiment of an implant system 10 used to reconnect ends of a severed or otherwise damaged vas deferens 2. The implant 10 includes first clamping device 12 and may be formed of a braid-like weave construct. The implant system 10 is implanted around the outside of the vas deferens 2. The first clamping device 12 helps keep the inner diameter of the vas deferens 2 open when the muscles contract and a tensile stress is applied to the tube that is joining the two ends of the vas deferens 2. When the vas deferens 2 contracts and thereby works to pull apart the two ends of the body lumen, the first clamping devices 12 expands to ensure the inner diameter remains open (FIG. 40).

Figure 41:
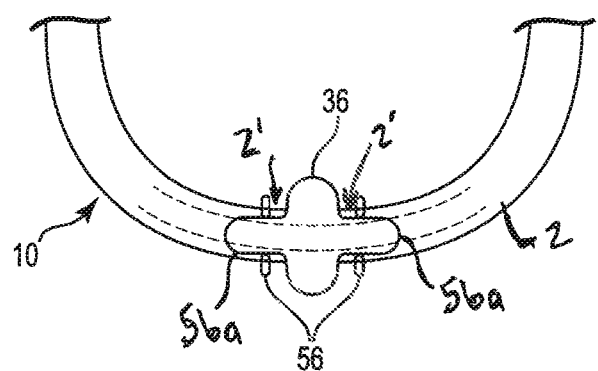

FIG. 41 shows an implant 10 further used to reconnect the ends of a severed or otherwise damaged vas deferens 2. The implant 10 comprises a joint 36 that joins to the end of the vas deferens 2 tube. The joint 36 has a fastener or like device 56 on each distal end 56a. The ends 56a can be inserted or otherwise provided around or within the body lumen. When the fastener 56 is connected to each end of the severed portions 2' of the vas deferens 2, the joint 36 allows fluid to flow through the vas deferens 2.

Figures 42A, 42B:
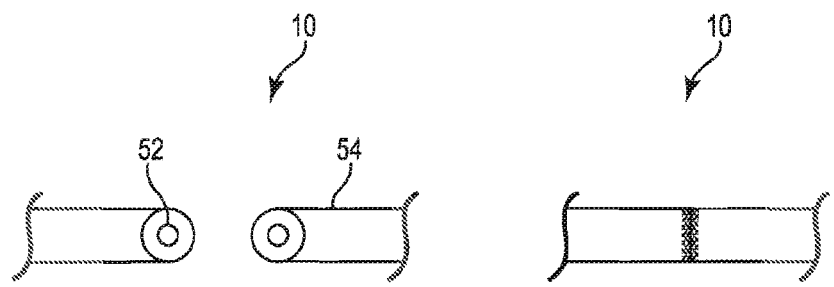
Figure 43:
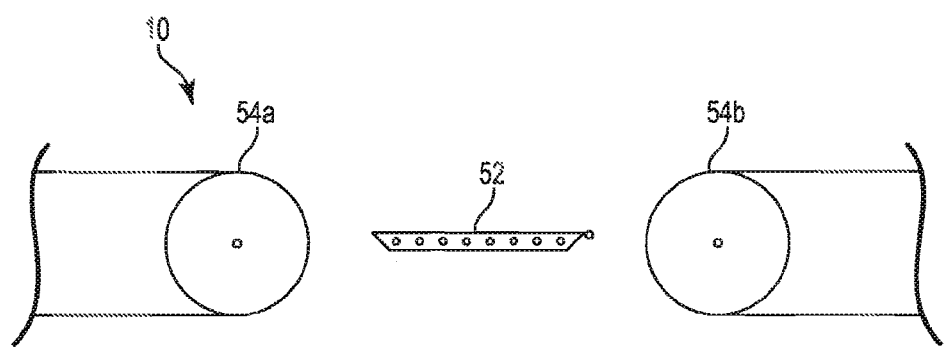

The embodiments of FIGS. 42-43 depict an implant system 10 used to reconnect a severed vas deferens. The implant system 10 has an inner diameter 52 and an outer diameter 54. The inner diameter 52 is deployed within the inner lumen of the vas deferens 2. The inner diameter 52 may have a slanted end portion to facilitate placement within the body lumen (FIG. 43). Additionally, the inner diameter 52 may have a series of small holes to facilitate incorporation in the tissue. The outer diameter device 54 is shaped to surround the lumen. The outer diameter device 54 may be comprised of one or more pieces 54a, 54b that each surround the top half or bottom half of the body lumen.

Figures 44A, 44B:
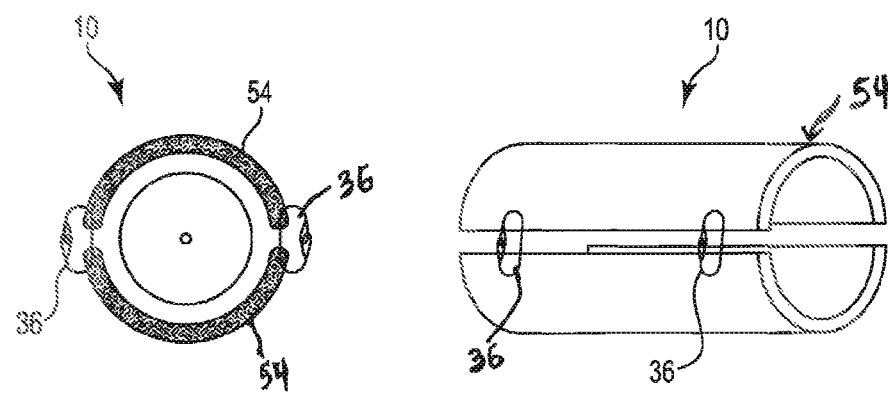

The one or more outer diameter devices 54 may be held together by one or more joints 36 (FIGS. 44a-44b). Joint 36 may be composed of a suture, clip, staple, or other device known in the art. The implant 10 may be constructed of an absorbable or non-absorbable material.

Figure 45:
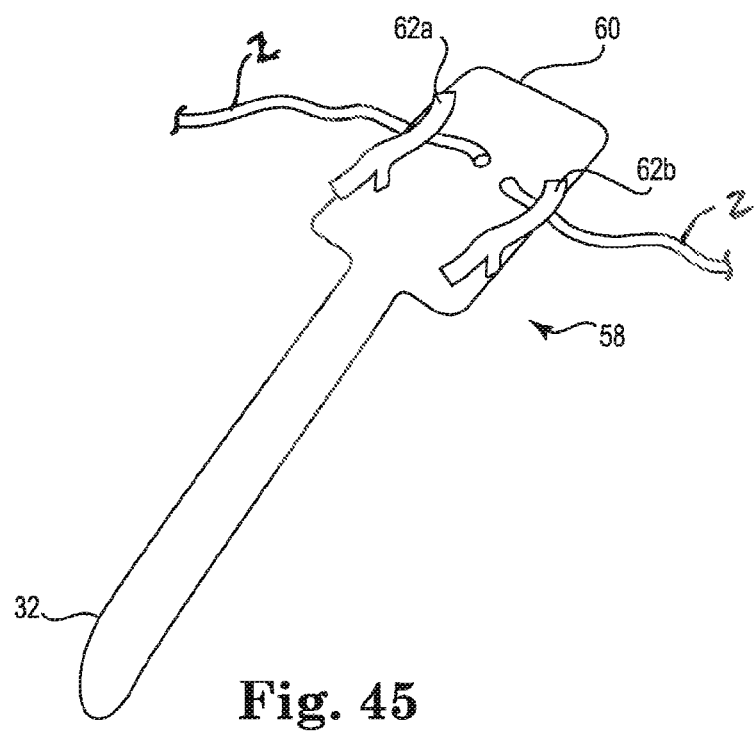

FIG. 45 illustrates an attachment instrument 58 for aiding in the reattachment of the vas deferens 2 in certain embodiments of the present invention. The attachment instrument 58 comprises a handle 32, a backboard 60, and one or more levers 62a, 62b. The one or more levers 62a, 62b may be spaced in parallel, a distance from each other on the backboard 60. The one or more levers 62a, 62b provide enough pressure on the vas deferens 2 to facilitate securement and resist movement, but not enough pressure to cause tissue necrosis or like damage. The vas deferens 2 is secured between the backboard 60 and the respective lever 62a, 62b. Reattachment procedures can be performed while the two vas deferens portions are secured in the instrument 58.

Figure 46A:
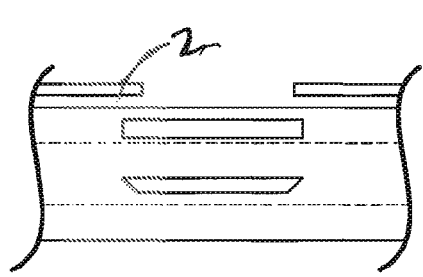
Figure 46B:
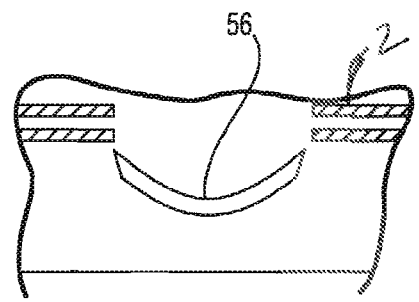
Figure 46C:
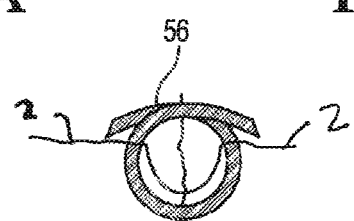

FIGS. 46a-c show a system of reattaching the vas deferens 2 in accordance with embodiments of the present invention. A fastener 56 is coiled when in a relaxed state and generally straight in an active state. The fastener 56 is threaded generally transverse through the vas deferens 2 to reconnect the two ends. Once connected, the fastener 56 takes on a coiled configuration to reattached the two ends of the body lumen. The fastener 56 may be implanted with the use of a tool having a cannula or like devices and techniques.

Figures 47A, 47B:
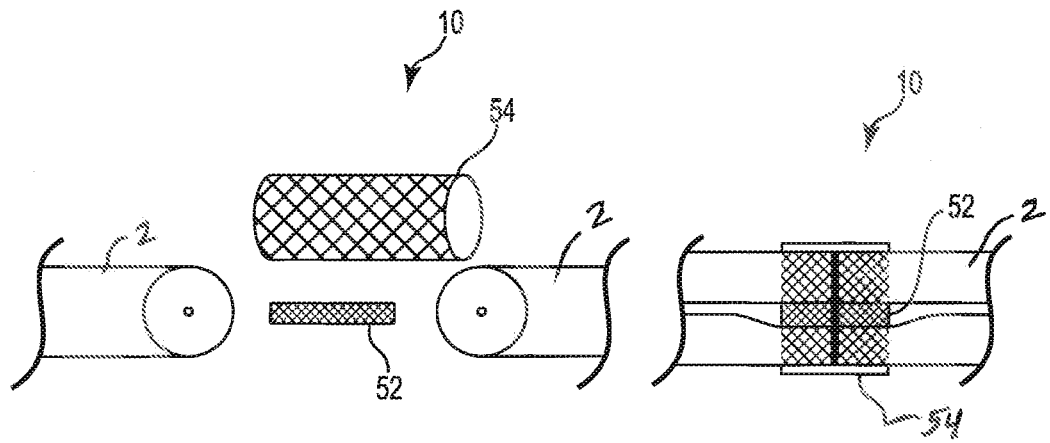

FIGS. 47a-47b illustrate another embodiment of the implant system 10 having an inner diameter tube 52 and an outer diameter tube 54. The inner diameter tube 52 is implanted within the vas deferens 2 and then heat set at a larger diameter than the actual inner diameter of the vas deferens 2. The inner diameter tube 52 can be made from an absorbable or non-absorbable woven, braided or like polymer material that is capable of expansion. Having the inner diameter tube 52 expand once implanted will resist migration and movement of the implant relative to the vas deferens 2. The outer diameter device 54 is implanted around the vas deferens 2 and then heat set at a smaller diameter than the actual outer diameter of the vas deferens 2 to provide securement.

Figure 48:
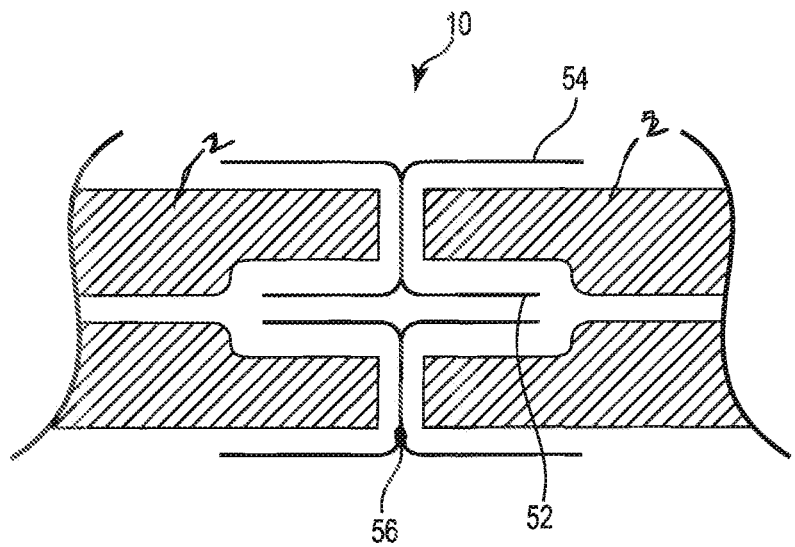

The embodiment of FIG. 48 includes an outer diameter device 54 and a fastener 56 to reconnect a severed vas deferens 2. The outer diameter device 54 can be shaped, for example, as a horizontal half of a toroid. The outer diameter device 54 can be placed around the end of each end of the vas deferens 2 portions. An inner diameter 52 of the device 10 is sized and shaped to keep the lumen of the vas deferens 2 open. A fastening device 56 secures the two outer diameter devices 54 to connect the vas deferens.

The various components, devices, systems and mechanism described herein can be constructed of known and compatible materials, such as acceptable polymers and metals. Further, all patents and publications referenced herein are hereby incorporated by reference in their entireties.

It will be understood that certain of the described structures, functions and operations of the above-described preferred embodiments are not necessary to practice the present invention and are included in the description simply for completeness of an exemplary embodiment or embodiments. It will also be understood that there may be other known structures, functions and operations ancillary to the typical surgical procedures that are not disclosed, but that can be implemented to practice the present invention. It is, therefore, to be understood that within the scope of the appended claims, the invention may be practiced other than as specifically described without actually departing from the spirit and scope of the present invention.

What is claimed is:
1. A vas deferens occlusion system, comprising:
   at least one clamping device with an elongated body including a longitudinal axis, an interior surface sized to receive an outer portion of a vas deferens, and an exterior surface with a radial surface feature extending into the elongated body and about the longitudinal axis; and
   at least one securement member operable with the radial surface feature of the at least one clamping device to apply pressure to the outer portion of the vas deferens and occlude an interior lumen of the vas deferens.

2. The system of claim 1, wherein the elongated body includes a generally tubular shape.

3. The system of claim 1, wherein the at least one securement member is a suture configured to extend circumferentially around the at least one clamping device.

4. The system of claim 1, wherein the radial surface feature includes at least one groove.

5. The system of claim 1, wherein the radial surface feature includes a plurality of grooves spaced apart along the elongated body, the elongated body includes a longitudinal gap, and each groove of the plurality of grooves is divided by the longitudinal gap.

6. A vas deferens occlusion system, comprising:
at least one clamping device including a generally tubular shape adapted to surround an outer portion of a vas deferens, and a plurality of radial grooves extending circumferentially around the generally tubular shape; and
at least one securement member operable with the plurality of radial grooves to facilitate securement of the at least one clamping device around the outer portion of the vas deferens and occlude an interior lumen of the vas deferens.

7. The system of claim 6, wherein the at least one securement member is a suture.

8. The system of claim 6, wherein the at least one clamping device includes a living hinge portion.

9. The system of claim 8, wherein the at least one clamping device includes a longitudinal gap.

10. The system of claim 6, further including a release mechanism to release the at least one securement member from the plurality of radial grooves.

11. The system of claim 6, further including an introducing tool to deploy the at least one clamping device around the vas deferens.

12. The system of claim 11, wherein the introducing tool includes a distal end portion adapted to engage the at least one clamping device.

13. The system of claim 6, wherein the at least one securement member is constructed at least in part of a shape memory material.

14. A vas deferens occlusion system, comprising:
at least one clamping device including a body with an interior surface defining an interior lumen sized to receive an outer portion of a vas deferens, and an exterior surface defining an exterior surface feature; and
at least one securement member configured to extend circumferentially around the body of the at least one clamping device, the at least one securement member being operable with the exterior surface feature to occlude an interior lumen of the vas deferens by selectively modifying the interior lumen of the at least one clamping device.

15. The system of claim 14, wherein the at least one clamping device is generally tubular.

16. The system of claim 14, wherein the at least one securement member is a suture, and the exterior surface feature includes at least one groove formed into an exterior surface of the at least one clamping device to receive at least a portion of the at least one securement member.

17. The system of claim 14, wherein the securement member is operable to selectively restrict or collapse the interior lumen of the at least one clamping device.

18. The system of claim 14, wherein the at least one clamping device comprises a longitudinal gap.

19. The system of claim 18, wherein the at least one clamping device has a living hinge portion.

20. The system of claim 18, wherein at least one clamping device includes a longitudinal axis, the interior lumen extends along the longitudinal axis, the exterior surface feature defines at least one sidewall perpendicular with the longitudinal axis, and the at least one securement member is operable with a portion of the at least one sidewall.

* * * * *